(12) United States Patent
Changezi et al.

(10) Patent No.: US 10,709,587 B2
(45) Date of Patent: Jul. 14, 2020

(54) BIFURCATED STENT AND DELIVERY SYSTEM

(71) Applicants: Hameem Unnabi Changezi, Grand Blanc, MI (US); Yousuf Chowdhary, Maple (CA)

(72) Inventors: Hameem Unnabi Changezi, Grand Blanc, MI (US); Yousuf Chowdhary, Maple (CA)

(73) Assignee: Hameem Unnabi Changezi, Grand Blanc, MI (US)

( * ) Notice: Subject to any disclaimer, the term of this patent is extended or adjusted under 35 U.S.C. 154(b) by 0 days.

(21) Appl. No.: 14/532,618

(22) Filed: Nov. 4, 2014

(65) Prior Publication Data

US 2015/0127084 A1    May 7, 2015

Related U.S. Application Data

(60) Provisional application No. 61/962,276, filed on Nov. 5, 2013.

(51) Int. Cl.
*A61F 2/856* (2013.01)
*A61F 2/954* (2013.01)

(52) U.S. Cl.
CPC .............. *A61F 2/856* (2013.01); *A61F 2/954* (2013.01)

(58) Field of Classification Search
CPC .. A61F 2/95; A61F 2/954; A61F 2/958; A61F 2002/065; A61F 2002/821; A61F 2230/006; A61F 2/82; A61F 2/844; A61F 2/852; A61F 2/856; A61F 2002/826; A61F 2002/828

USPC .................................. 623/1.11, 1.35, 110
See application file for complete search history.

(56) References Cited

U.S. PATENT DOCUMENTS

| | | | | |
|---|---|---|---|---|
| 6,096,073 A | * | 8/2000 | Webster | A61F 2/91 623/1.16 |
| 6,165,195 A | * | 12/2000 | Wilson | A61F 2/856 606/108 |
| 6,325,826 B1 | * | 12/2001 | Vardi | A61F 2/82 623/1.15 |
| 6,520,988 B1 | * | 2/2003 | Colombo | A61F 2/856 623/1.11 |
| 6,676,696 B1 | * | 1/2004 | Marotta | A61F 2/82 606/200 |
| 6,692,483 B2 | * | 2/2004 | Vardi | A61F 2/954 604/284 |

(Continued)

OTHER PUBLICATIONS

Chen et al., "Bifurcation Stenting", pp. 27-49.

*Primary Examiner* — Dianne Dornbusch
(74) *Attorney, Agent, or Firm* — White and Williams LLP (57) ABSTRACT

A stent system is provided for stenting a bifurcated vessel structure having a parent vessel and a daughter vessel. The stent system has a parent vessel stent and a daughter vessel stent. The parent vessel stent has a substantially tubular body that is configured to be deployed into the parent vessel. This body has an angular flap that is openable to extend into the daughter vessel. The daughter vessel stent has a substantially tubular body that is configured to be deployed through the flap in the parent vessel stent into the daughter vessel. The daughter vessel stent has an angled tail portion that is configured to overlap with the flap of the parent vessel stent when both stents are deployed in the vessel structure. A method of stenting using this system is also provided.

12 Claims, 10 Drawing Sheets

(56) References Cited

U.S. PATENT DOCUMENTS

| | | | | |
|---|---|---|---|---|
| 7,220,275 B2* | 5/2007 | Davidson | A61F 2/82 | 623/1.35 |
| 7,485,140 B2* | 2/2009 | Eidenschink | A61F 2/856 | 623/1.15 |
| 8,348,991 B2* | 1/2013 | Weber | A61F 2/856 | 623/1.15 |
| 8,747,456 B2* | 6/2014 | Baim | A61F 2/954 | 623/1.11 |
| 2001/0003161 A1* | 6/2001 | Vardi | A61F 2/954 | 623/1.11 |
| 2001/0044622 A1* | 11/2001 | Vardi | A61F 2/954 | 606/1 |
| 2002/0035389 A1* | 3/2002 | Richter | A61F 2/07 | 623/1.11 |
| 2002/0072790 A1* | 6/2002 | McGuckin, Jr. | A61F 2/07 | 623/1.12 |
| 2002/0116047 A1* | 8/2002 | Vardi | A61F 2/856 | 623/1.11 |
| 2002/0173840 A1* | 11/2002 | Brucker | A61F 2/95 | 623/1.16 |
| 2002/0193873 A1* | 12/2002 | Brucker | A61F 2/954 | 623/1.35 |
| 2003/0074047 A1* | 4/2003 | Richter | A61F 2/07 | 623/1.11 |
| 2003/0097169 A1* | 5/2003 | Brucker | A61F 2/856 | 623/1.11 |
| 2004/0088007 A1* | 5/2004 | Eidenschink | A61F 2/856 | 607/1 |
| 2004/0138737 A1* | 7/2004 | Davidson | A61F 2/82 | 623/1.35 |
| 2004/0225345 A1* | 11/2004 | Fischell | A61F 2/954 | 623/1.11 |
| 2004/0267352 A1* | 12/2004 | Davidson | A61F 2/82 | 623/1.15 |
| 2005/0102023 A1* | 5/2005 | Yadin | A61F 2/856 | 623/1.15 |
| 2006/0036315 A1* | 2/2006 | Yadin | A61F 2/856 | 623/1.35 |
| 2006/0100694 A1* | 5/2006 | Globerman | A61F 2/856 | 623/1.35 |
| 2006/0173528 A1* | 8/2006 | Feld | A61F 2/856 | 623/1.15 |
| 2006/0287712 A1* | 12/2006 | Eidenschink | A61F 2/856 | 623/1.35 |
| 2007/0016279 A1* | 1/2007 | Konstantino | A61F 2/954 | 623/1.11 |
| 2007/0050016 A1* | 3/2007 | Gregorich | A61F 2/856 | 623/1.35 |
| 2007/0055356 A1* | 3/2007 | Eidenschink | A61F 2/07 | 623/1.25 |
| 2007/0055362 A1* | 3/2007 | Brown | A61F 2/856 | 623/1.35 |
| 2007/0203562 A1* | 8/2007 | Malewicz | A61F 2/954 | 623/1.11 |
| 2007/0208415 A1* | 9/2007 | Grotheim | A61F 2/856 | 623/1.16 |
| 2007/0208419 A1* | 9/2007 | Meyer | A61F 2/856 | 623/1.35 |
| 2007/0225796 A1* | 9/2007 | Yadin | A61F 2/856 | 623/1.16 |
| 2008/0208307 A1* | 8/2008 | Ben-Muvhar | A61F 2/91 | 623/1.11 |
| 2008/0221655 A1* | 9/2008 | Miller | A61F 2/856 | 623/1.11 |
| 2009/0012599 A1* | 1/2009 | Broome | A61F 2/856 | 623/1.16 |
| 2009/0182409 A1* | 7/2009 | Feld | A61F 2/856 | 623/1.11 |
| 2009/0240318 A1* | 9/2009 | Chalekian | A61F 2/856 | 623/1.16 |
| 2009/0259293 A1* | 10/2009 | Moloney | A61F 2/856 | 623/1.16 |
| 2010/0030316 A1* | 2/2010 | Prindle | A61F 2/856 | 623/1.11 |
| 2010/0049548 A1 | 2/2010 | Kubota | | |
| 2010/0056297 A1 | 3/2010 | Roach et al. | | |
| 2010/0106241 A1* | 4/2010 | Park | A61F 2/82 | 623/1.35 |
| 2010/0137973 A1* | 6/2010 | Sutermeister | A61F 2/856 | 623/1.15 |
| 2010/0152830 A1* | 6/2010 | Weber | A61F 2/856 | 623/1.11 |
| 2010/0324664 A1* | 12/2010 | Holzer | A61F 2/856 | 623/1.35 |
| 2011/0087318 A1* | 4/2011 | Daugherty | A61F 2/07 | 623/1.13 |
| 2012/0221094 A1* | 8/2012 | Cunningham | A61F 2/07 | 623/1.12 |
| 2012/0271401 A1* | 10/2012 | Bruszewski | A61F 2/07 | 623/1.15 |
| 2012/0290069 A1* | 11/2012 | Ivancev | A61F 2/07 | 623/1.13 |
| 2013/0282102 A1* | 10/2013 | Peterson | A61F 2/07 | 623/1.13 |
| 2015/0005868 A1* | 1/2015 | Koskas | A61F 2/07 | 623/1.13 |

\* cited by examiner

BIFURCATED STENT AND DELIVERY SYSTEM

CROSS-REFERENCE TO RELATED APPLICATIONS

This application claims the benefit of U.S. Provisional Patent Application No. 61/962,276, filed Nov. 5, 2013 and entitled "Bifurcated Stent and Delivery System," which is incorporated herein by reference in its entirety.

FIELD OF INVENTION

The field of invention is generally related to medical stents and related delivery systems. More specifically, the invention relates to specifically designed stents and techniques for deploying these stents into vessel bifurcations, allowing for better coverage of the atherosclerotic lesion and preservation of the side-branch ostium with proper stent strut apposition to the vessel walls. The invention overcomes many of the limitations of the previous art.

BACKGROUND

A stent is a mesh 'tube' inserted into a natural passage/conduit in the body to remove or counteract a disease-induced, localized flow constriction. The term may also refer to a tube used to temporarily hold such a natural conduit open to allow access for surgery.

Most of the time, stents are used to treat conditions that result when arteries become narrow or blocked. When a stent is placed into the body, the procedure is called stenting. A stent is placed in an artery as part of a procedure called angioplasty. Angioplasty restores blood flow through narrow or blocked arteries. A stent helps support the inner wall of the artery after angioplasty.

Stents are generally tubular devices for insertion into body lumens. Balloon expandable stents require mounting over a balloon, positioning, and inflation of the balloon to expand the stent radially outward. Self-expanding stents expand into place when unconstrained, without requiring assistance from a balloon. A self-expanding stent is biased so as to expand upon release from the delivery catheter. Some stents may be characterized as hybrid stents which have some characteristics of both self-expandable and balloon expandable stents. Almost all stents used in the treatment of coronary atherosclerosis are balloon expandable. Self-expandable stents are generally used in larger blood vessel in the limbs and periphery.

There are different kinds of stents. Stents usually are made of metal mesh of various metals and alloy combinations. Some stents are a plastic mesh-like material, and some stents are a combination of metal and synthetic lining material (for example PTFE-Polytetrafluoroethylene) and are called stent grafts and are used in larger arteries.

An intraluminal coronary artery stent is a small, balloon-expandable, metal mesh tube that is placed inside a coronary artery to prevent the artery from re-closing. The metal portion of the structure is called a strut and the open portion of the mesh between struts is called a cell. Re-narrowing of arteries at the site of stent deployment has been addressed with medicine coated stents, called drug-eluting stents. Like other coronary artery stents, it is left permanently in the artery.

Stents may be constructed from a variety of materials such as stainless steel, Elgiloy®, nitinol, shape memory polymers, etc. Stents may also be formed in a variety of manners as well. For example a stent may be formed by etching or cutting the stent pattern from a tube or section of stent material; a sheet of stent material may be cut or etched according to a desired stent pattern whereupon the sheet may be rolled or otherwise formed into the desired tubular or bifurcated tubular shape of the stent; one or more wires or ribbons of stent material may be braided or otherwise formed into a desired shape and pattern.

Repair of coronary vessels that are diseased at a bifurcation is particularly challenging since the stent must be precisely positioned, provide adequate coverage of the disease, provide access to any diseased area located distal to the bifurcation, and maintain vessel patency in order to allow adequate blood flow to reach the myocardium.

Currently employed techniques have results that are less favorable than stenting results for lesions that do not involve bifurcations. The most commonly employed technique is to introduce guide-wires into the main blood vessel (parent-vessel) and the side branch (daughter-vessel). The ostium of the daughter-vessel is treated with balloon angioplasty and then a stent is deployed in the parent-vessel as if there was no bifurcation involvement. The hope is to have a stent cell line up with the ostium of the daughter-vessel resulting in unobstructed flow. However, in reality this is not always the case and stent struts usually are left in the ostium increasing the risk of acute and subacute stent thrombosis. Also promotion of neointimal growth onto the unopposed struts can result in renarrowing. A daughter-vessel is in effect "jailed" by the stent and blood flow can continue to be compromised results in inadequate treatment.

Another phenomenon that is of concern in treatment of bifurcations is plaque shift. When a balloon or a stent is deployed in an artery, the plaque is compressed against the vessel wall. However, if there is a side branch ostium that is being stented across, plaque just beyond the bifurcation moves and shifts into the side branch resulting in worsening of the narrowing in this vessel. Plaque shift is of greatest concern when the plaque is located on the carina or the apex of the bifurcation.

Alternatively, access into a jailed vessel can be attained by carefully placing a guide-wire through the stent, and subsequently tracking a balloon catheter through the stent struts. The balloon could then be expanded, thereby deforming the stent struts and forming an opening into the previously jailed vessel. The cell to be spread apart must be randomly and blindly selected by re-crossing the deployed stent with a guide-wire. The drawback with this approach is that there is no way to determine or guarantee that the main-vessel stent struts are properly oriented with respect to the side branch or that an appropriate stent cell has been selected by the wire for dilatation. The aperture created often does not provide a clear opening and creates a major distortion in the surrounding stent struts. A further drawback with this approach is that there is no way to tell if the main-vessel stent struts have been properly oriented and spread apart to provide a clear opening for stenting the side branch vessel. This technique also causes stent deformation to occur in the area adjacent to the carina, pulling the stent away from the vessel wall and partially obstructing flow in the originally non-jailed vessel. Deforming the stent struts to regain access into the previously jailed vessel is also a complicated and time consuming procedure associated with attendant risks to the patient and is typically performed only if considered an absolute necessity. The deformation of the contralateral struts has been addressed by doing a simultaneous inflation with two balloons, one being placed in the parent and the other in the daughter-vessel. The inability to place a guide-wire through the jailed lumen in a timely fashion could restrict blood supply and begin to precipitate symptoms of angina, resulting in myocardial infarction or even cardiac arrest.

Other methods employed include a "T-stent" procedure. This involves implanting a stent in the daughter-vessel ostium followed by stenting of the parent-vessel across the daughter-vessel. Subsequently deforming the struts as previously described, to allow blood flow and access into the daughter-vessel. Alternatively, a stent is deployed in the parent-vessel followed by subsequent strut deformation as previously described, and finally a stent is placed into the daughter-vessel. Stent deployment in the ostium of the daughter-vessel may be necessary if there is a significant plaque burden at the bifurcation and involves the ostium of the daughter-vessel. Conversely stenting of the daughter-vessel may be required to treat a possible dissection created by the initial angioplasty. T-stenting would theoretically be useful in situations where the angle between the parent and daughter vessels is 90-degrees. This is rarely the case in real life and the alignment of the stent in the daughter-vessel with the apex of the carina results in inadequate coverage of the ostium. Alignment of the stent to the beginning of the side branch ostium results in protrusion of stent struts into the parent-vessel lumen. Both scenarios increase the risk of subsequent complications and renarrowing.

In another prior art method for treating bifurcated vessels, commonly referred to as the "Culotte technique," the side branch vessel is first stented so that the stent protrudes into the main or parent vessel. A dilatation is then performed in the main or parent vessel to open and stretch the stent struts extending across the lumen from the side branch vessel. Thereafter, a stent is implanted in the main branch so that its proximal end overlaps with the already-stented side branch vessel. One of the drawbacks of this approach is that the orientation of the stent elements protruding from the side branch vessel into the main vessel is completely random. In addition excessive metal coverage exists from overlapping strut elements in the parent vessel proximal to the carina area. Furthermore, the deployed stent must be recrossed with a wire and arbitrarily selecting a particular stent cell. When dilating the main vessel the stent struts are randomly stretched, thereby leaving the possibility of restricted access, incomplete lumen dilatation, and major stent distortion.

In another prior art procedure, known as "kissing" stents, a stent is implanted in the main vessel with a side branch stent partially extending into the main vessel creating a double-barrelled lumen of the two stents in the main vessel distal to the bifurcation. Another prior art approach includes a so-called "trouser legs and seat" approach, which includes implanting three stents, one stent in the side branch vessel, a second stent in a distal portion of the main vessel, and a third stent, or a proximal stent, in the main vessel just proximal to the bifurcation.

All of the above-mentioned examples of stent deployment techniques suffer from the same problems and limitations. There can be uncovered intimal surface segments on the daughter-vessel between the stented segment and the parent-vessel or there is excessive coverage in the parent vessel proximal to the bifurcation. An uncovered intimal surface with a possible dissection flap or uncompressed plaque will increase the risk for sub-acute thrombosis, and the increased risk of the development of restenosis. Further, where portions of the stent are left unapposed within the lumen, the risk for subacute thrombosis or the development of restenosis is increased also. The prior art stents and delivery assemblies for treating bifurcations are difficult to use and deliver making successful placement nearly impossible.

Further, even where placement has been successful, the side branch vessel can be "jailed" or covered so that there is impaired access to the stented area for subsequent intervention.

Prior art Tryton bifurcation stent with trizone technology suffers from the same limitation of requiring to recross the stent struts of the parent-vessel stent with an arbitrary selection of a cell and subsequent deformation along with all its limitations as previously described.

One prior art stent that is specifically designed for bifurcations in the petal stent from Boston Scientific. This has a specifically designed collar which expands radially into the ostium of the daughter vessel. The collar is designed as radially placed struts covering the entire perimeter of the ostium. The symmetry of the collar is believed to be a drawback as most bifurcations have non-90° take off angles, and so the collar would create an unnecessary and excessive crowding or deformation of struts in the ostium.

The key element in the successful treatment of bifurcation with current art/technology is the simultaneous "kissing" balloon inflation. Successful placement of a guide-wire through the struts of the stent in the parent-vessel is essential for this to occur. Inability to cross with a guide-wire into the daughter-vessel would leave stent struts in the ostium and unopposed to the intimal surface. The present invention solves these and other problems as will be shown.

SUMMARY

The prior art deficiencies and other problems associated with bifurcated stents and related delivery systems are overcome by the disclosed invention. It is an objective of the present invention to provide a bifurcated stent system that is easily delivered and deployed with precise positioning at a bifurcation. The invention simplifies the bifurcation stent delivery system eliminating the crucial and often failed step of recrossing with a guide-wire. It also eliminates the issue of uncovered intimal surface in the daughter-vessel and strut protrusion in the parent-vessel.

The preferred embodiment of the invention provides a bifurcated stent and related delivery system that allows retaining the guide wire in the daughter branch during the stent deployment in the parent vessel. It provides for coverage of the area of the ostium of the daughter vessel with precise placement of the parent vessel stent. The system provides for precise placement of the daughter vessel stent as well.

In another embodiment of the invention, the side branch (daughter vessel) stent could be used for placement in the ostial location of a single vessel.

Other embodiments of the invention with variation in length and diameter in conjunction with other standard stents can be utilised for treatment of plaque in the left main artery location effectively dealing with the ostial placement of the left main stent and as well as the left main/left anterior descending and left circumflex coronary artery bifurcation.

In summary the preferred embodiment of the invention provides a bifurcated stent and related delivery system that is deliverable and effectively overcomes the limitations of the prior art. Accurate placement, proper strut apposition, adequate coverage of intimal surfaces and preservation of the geometry of the side branch ostium will result in proper treatment of plaque at or near bifurcations. Part of the system can be used for accurate placement of stents in the ostial location.

According to a first aspect of the invention, a stent system is provided for stenting a bifurcated vessel structure having a parent vessel and a daughter vessel. The stent system has a parent vessel stent and a daughter vessel stent. The parent vessel stent has a substantially tubular body that is configured to be deployed into the parent vessel. This body has an angular flap that is openable to extend into the daughter vessel. The daughter vessel stent has a substantially tubular body that is configured to be deployed through the flap in the parent vessel stent into the daughter vessel. The daughter vessel stent has an angled tail portion that is configured to overlap with the flap of the parent vessel stent when both stents are deployed in the vessel structure.

Preferably, the parent vessel stent includes an introduction site proximate to a leading edge of the body of the parent vessel stent, which allows for passage of a daughter vessel guide wire on the inside of the stent along a luminal side thereof.

Preferably, the parent vessel stent includes a radio-opaque marker proximate to this introduction site.

The parent vessel stent may be pre-loaded (or later wired with) a parent vessel guide wire disposed substantially coaxially inside the body of the parent vessel stent.

Preferably, the flap includes at least one radio-opaque marker.

In the preferred embodiment, the flap has struts allowing opening of the flap in one direction. Preferably, the struts extend only on one side and do not form a collar around an ostium of the daughter vessel when opened. Preferably, the flap has struts forming a periphery around the flap. The flap is preferably a specially designed area in the parent vessel stent with a strut configuration that is different from the strut configuration of the main body of the parent vessel stent. The strut configuration allows the segment to be opened up as a flap providing coverage along a proximal end of the daughter vessel. Preferably, there are no struts along the distal edge of the ostium of the daughter vessel with the edge of the flap segment of the patient's vessel being aligned to it.

In the preferred embodiment, the parent vessel stent has a spine which also extends along a central portion of the flap.

The parent vessel stent may be pre-loaded (or may be later provided) with a balloon for deployment of the parent vessel stent.

In certain embodiments, at least one of the parent vessel stent or the daughter vessel stent may contain a drug, or may be configured to elute a drug.

Preferably, the daughter vessel stent includes a side hole proximate to a trailing edge of the body of the daughter vessel stent for passage of a parent vessel guide wire. Preferably, the side hole is defined radially opposite the angled tail portion of the daughter vessel stent.

Preferably, the daughter vessel stent includes a radio-opaque marker proximate to the side hole.

The daughter vessel stent may be pre-loaded (or later wired with) a daughter vessel guide wire disposed substantially coaxially inside the body of the daughter vessel stent.

According to a second aspect of the invention, a method is provided for stenting a bifurcated vessel structure having a parent vessel and a daughter vessel and where the daughter vessel branches from the parent vessel at an angle. The daughter vessel has an ostium where it joins the parent vessel. The ostium in turn has a proximal edge and a distal edge. The method comprises:

(1) inserting a parent vessel guide wire and a daughter vessel guide wire into the parent and daughter vessels, respectively;

(2) loading a parent vessel stent on both wires, such that the parent vessel guide wire is substantially coaxial with the parent vessel stent; and such that the daughter vessel guide wire runs generally inside the parent vessel stent along its daughter vessel luminal side and emerges at a side hole in the parent vessel stent;

(3) positioning the parent vessel stent with the daughter vessel guide wire at the distal edge of the daughter vessel ostium;

(4) deploying the parent vessel stent with a first balloon;

(5) deploying a side flap formed in the parent vessel stent into the ostium of the daughter vessel using a second balloon mounted on the daughter vessel guide wire;

(6) loading a daughter vessel stent on the daughter vessel guide wire and inserting the parent vessel guide wire such that the parent vessel guide wire runs through a side hole in the daughter vessel stent, the daughter vessel guide wire being generally coaxial with the daughter vessel stent;

(7) positioning the daughter vessel stent with the parent vessel guide wire at the distal edge of the ostium of the daughter vessel; and (8) deploying the daughter vessel stent with a third balloon.

Importantly, once deployed, the flap of the deployed parent vessel stent and an angled side wall of the deployed daughter vessel stent overlap and are apposed at least in part with the proximate edge of the ostium.

The method may further include predilating one or both vessels prior to inserting the parent vessel guide wire.

The method may further include removing plaque from one or both vessels prior to inserting the parent vessel guide wire.

The method may further include performing a kissing balloon inflation with a fourth balloon after deploying the daughter vessel stent for further shaping of the bifurcation.

DETAILED DESCRIPTION

Before embodiments of the invention are explained in detail, it is to be understood that the invention is not limited in its application to the details of the examples set forth in the following descriptions or illustrated drawings. The invention is capable of other embodiments and of being practiced or carried out for a variety of applications and in various ways. Also, it is to be understood that the phraseology and terminology used herein is for the purpose of description and should not be regarded as limiting. The system includes balloon expandable stents.

The preferred embodiment of the invention provides a bifurcated stent and related delivery system that is deliverable and effectively overcomes the limitations of the prior art. Accurate placement, proper strut apposition, adequate coverage of intimal surfaces and preservation of the geometry of the side branch ostium will result in proper treatment of plaque at or near bifurcations. Part of the system can be used for accurate placement of stents in the ostial location.

In the preferred embodiment of the invention, the following steps are taken for the deployment of the bifurcation stents of the invention:
1. Wire both vessels.
2. Predilate both lesions. Calcified lesions may require debulking/atherectomy.
3. Backload "main vessel stent" on the wires, with the wire from the daughter-vessel being introduced through the side-hole in the flap area (FIGS. 5, 6 and 7).
4. Position the stent in the parent-vessel with daughter-vessel wire at the distal edge of its ostium (FIG. 12).
5. Deploy stent (FIG. 13) and remove stent delivery balloon.
6. Deploy the "side-flap" further by using a balloon on the side-branch wire (FIG. 14).
7. Load "side branch stent", this time with the wire from the parent vessel in the "side-hole" (FIG. 10).
8. Position the stent with the wire from the "side-hole" (parent branch) at the edge of the ostium of the side branch (FIG. 15).
9. Deploy stent (FIG. 16) and remove the stent delivery balloon.
10. Perform "kissing" balloon inflation if needed for further shaping of the bifurcation.

FIGS. 1 through 4 demonstrate the various shortcomings of the prior art that are overcome by the present invention. Please note that not all permutations of prior art are presented here. However, the common issues with prior art include:
1. Inadequate coverage of vessel intima (extent dependant on technique employed).
2. Strut protrusion into adjacent vessel lumen.
3. Need to cross cells of a stent with a guide wire after its deployment. This is a very crucial and often limiting step in the treatment of bifurcation lesions with prior art.

Note that in the present system, wires cross through a flap of a deployed stent and through a marked introduction site, but do not need to be inserted through cells (between struts).

Figure 1:
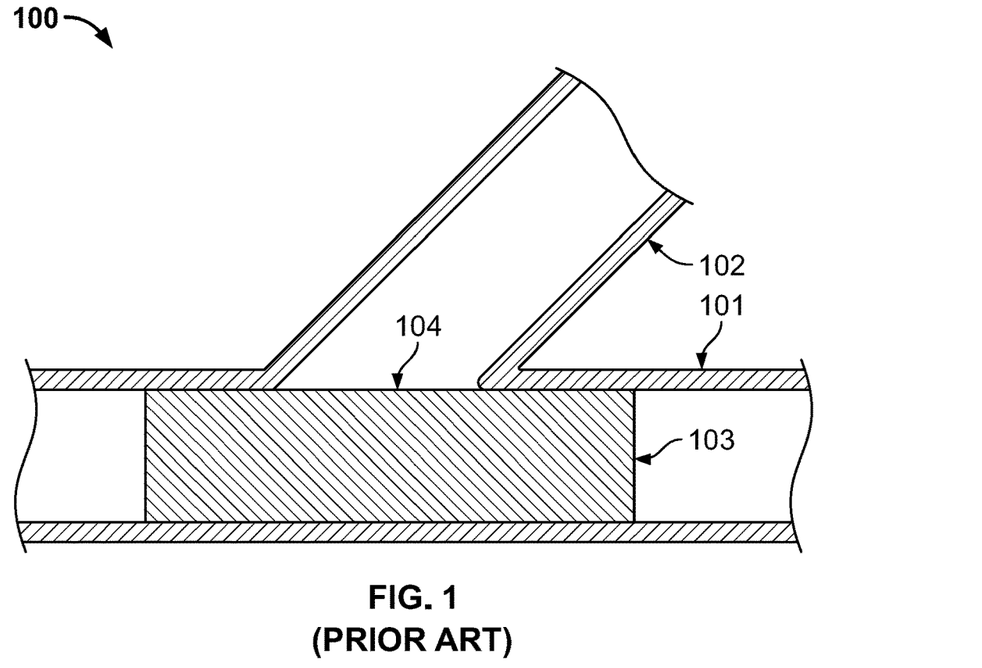
FIG. 1 is a simplified vessel diagram showing deployment of a parent vessel stent with jailing effect across side branch (prior art).

FIG. 1 shows prior art with deployment 100 of a stent 103 in the parent vessel 101, across the ostium of the side branch 102. This has the problems of jailing of the side branch 102 and also leaving unopposed stent struts 104. These result in poor long term outcomes.

Figure 2A:
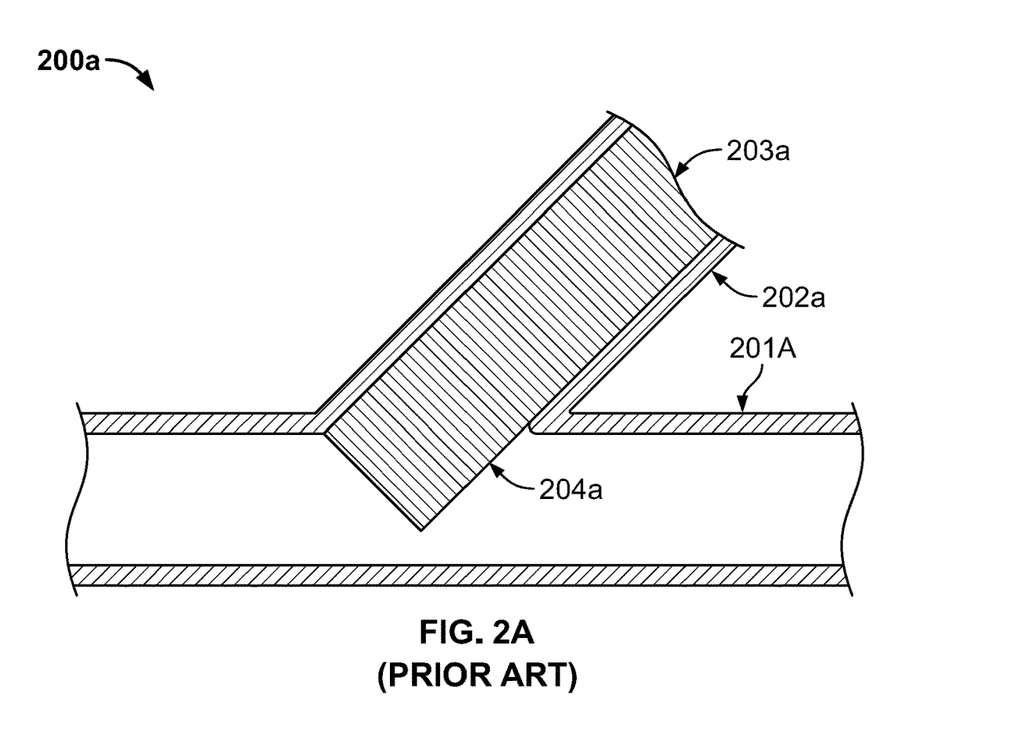
FIG. 2a is a simplified vessel diagram showing deployment of a daughter vessel stent with protrusion into parent vessel (prior art).

FIG. 2a shows deployment 200a of a stent 203a in the daughter vessel (side branch) 202a. The stent is aligned to the proximal edge of the ostium and has the problem of stent struts 204a protruding into the lumen of the parent vessel (main branch) 201a.

Figure 2B:
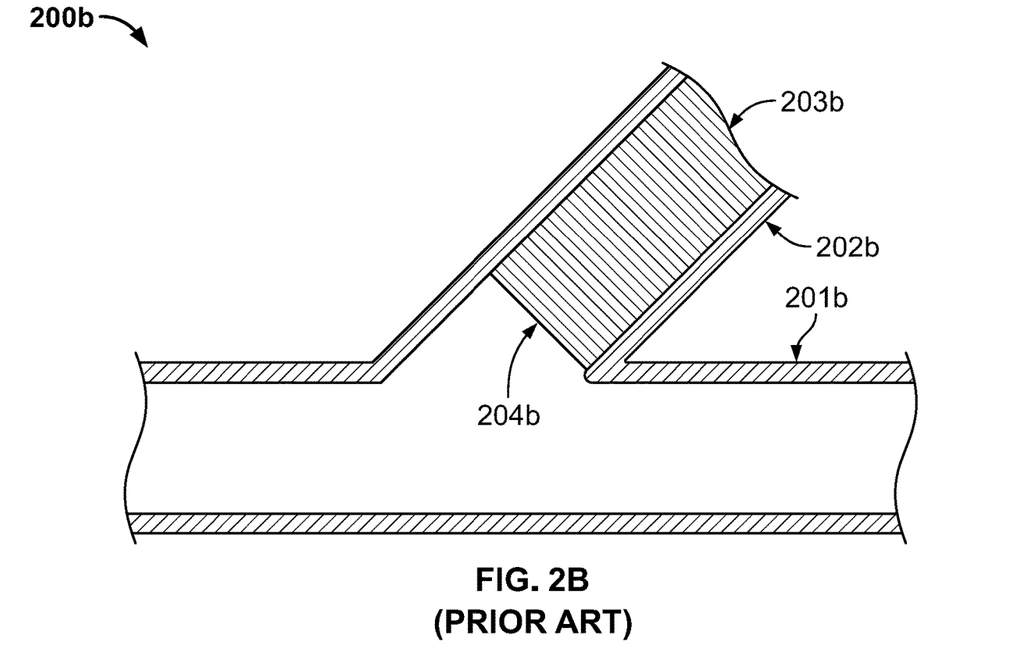
FIG. 2b is a simplified vessel diagram showing deployment of a daughter vessel stent with uncovered daughter vessel intima (prior art).

FIG. 2b shows deployment 200b of a stent 203b in the daughter vessel (side branch) 202b. The stent is aligned to the distal edge of the ostium and has the problem of leaving part of the intima of the daughter vessel uncovered 204b.

Figure 3:
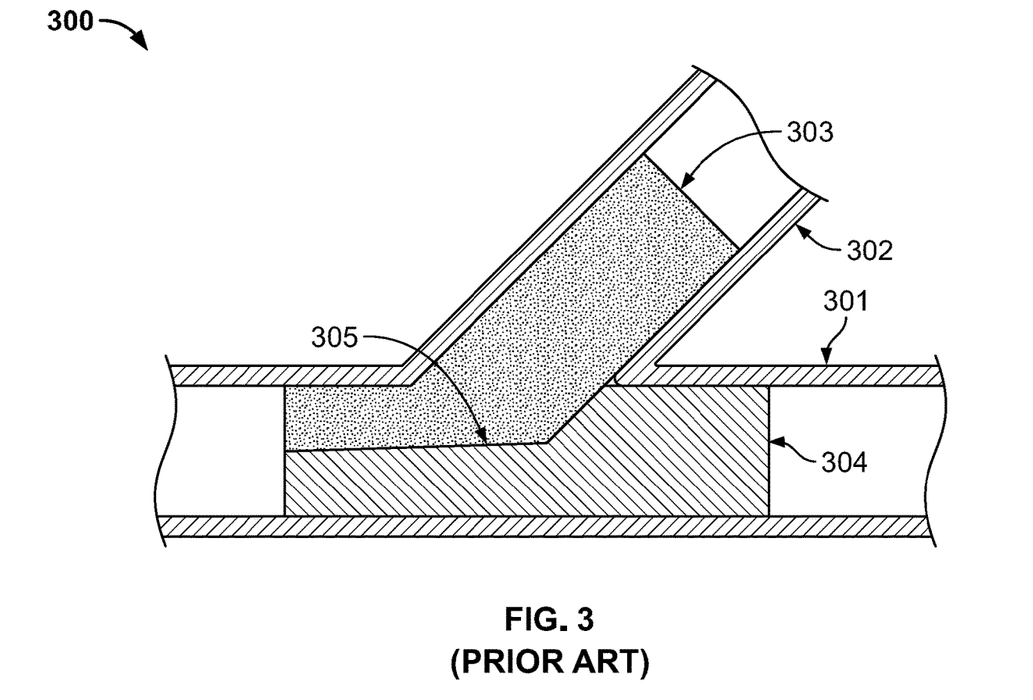
FIG. 3 is a simplified vessel diagram showing deployment using stent culotte technique (prior art).

FIG. 3 shows deployment 300 using the stent culotte technique (a suboptimal two-stent prior art technique for bifurcated vessels). Stents 303 and 304 are placed simultaneously in the daughter 302 and parent 301 vessels respectively. This results in unopposed stent struts 305 in the parent (main) vessel 301.

Figure 4:
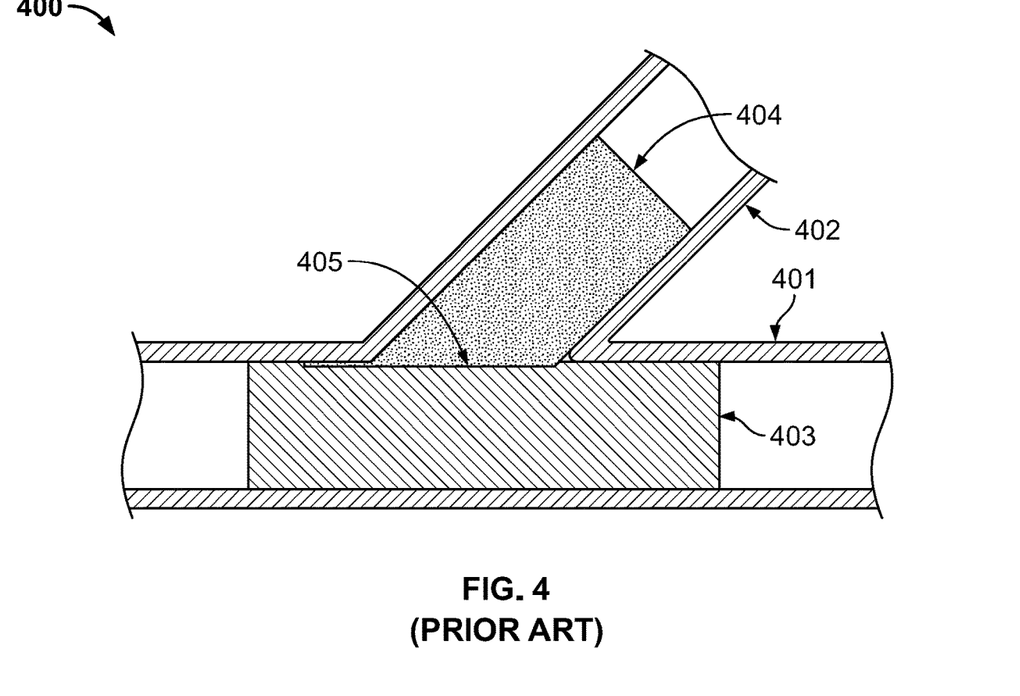
FIG. 4 is a simplified vessel diagram showing deployment using stent crush technique (prior art).

FIG. 4 shows deployment 400 using the stent crush technique (another suboptimal two-stent prior art technique for bifurcated vessels). In this technique stent 404 is placed in the daughter vessel 402 first with the stent deliberately left protruding in the parent vessel. This stent is then crushed with deployment of a stent 403 in the parent vessel 401. This results in a double layer of stent struts 405 across the daughter vessel ostium. It also has the problem of making it difficult to navigate the wire into the daughter vessel (side branch) through the struts of not one but two stents.

FIGS. 5 through 11 show at least one embodiment of the present system with the salient features of its various components, primarily the parent vessel stent (main artery) with the "flap" area and the daughter vessel (side branch) stent with the angled proximal edge.

Figure 5:
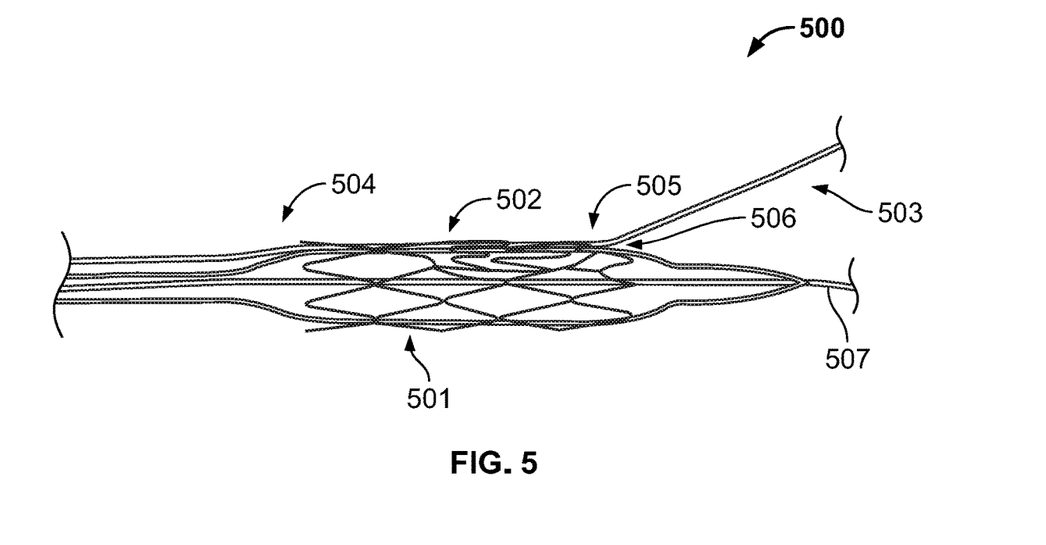
FIG. 5 is a schematic diagram of a parent vessel stent system according to an embodiment of the present invention.

FIG. 5 shows the basic design of the parent vessel system 500 with parent vessel stent 501 with "flap" area 502. Advantages include keeping the daughter vessel guide wire 503 on the luminal side 504 of the stent thereby eliminating the need of trying to recross the struts of the stent in the parent vessel while the parent vessel guide wire 507 is coaxial with the parent vessel stent 501. Also location of the introduction site of the daughter vessel wire 505 in conjunction with the radio-opaque markers on the stent 506 allows positioning of the "flap" area at the ostium of the daughter vessel. The "flap" 502 in combination with the angled proximal edge of the daughter vessel (side branch) stent (not shown in FIG. 5) eliminates the uncovered intimal portion of the daughter vessel (i.e. the problem shown in FIG. 2b, at 204b).

Figure 6:
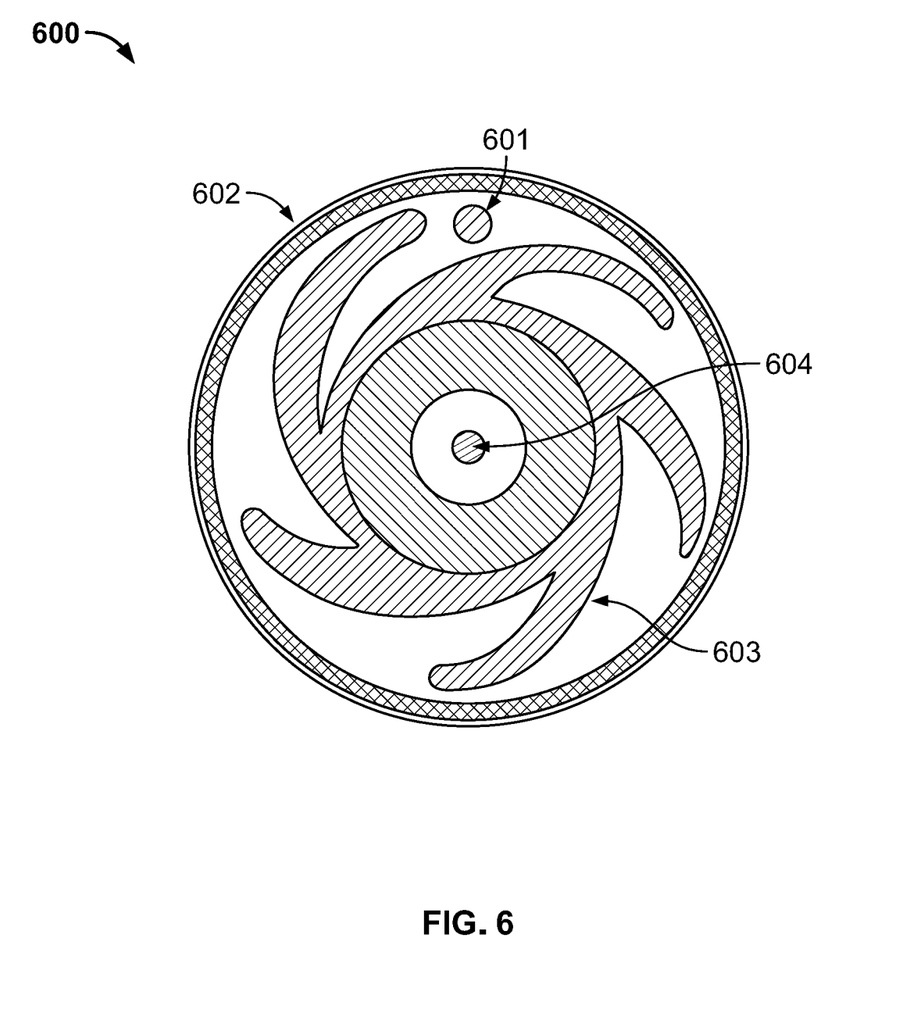
FIG. 6 is a simplified sectional view of the parent vessel stent system of FIG. 5 showing guide wires and deployment balloon.

FIG. 6 shows a schematic of the cross section of the parent vessel stent catheter/stent system 600. This cross section is proximal to the introduction site (reference character 505 in FIG. 5) of the daughter vessel guide wire 601, showing its location on the luminal side of the stent 602. The parent vessel guide wire 604 is coaxial in the center. The daughter vessel guide wire 601 is not coaxial and is in between the stent 602 and the deployment balloon 603.

Figure 7:
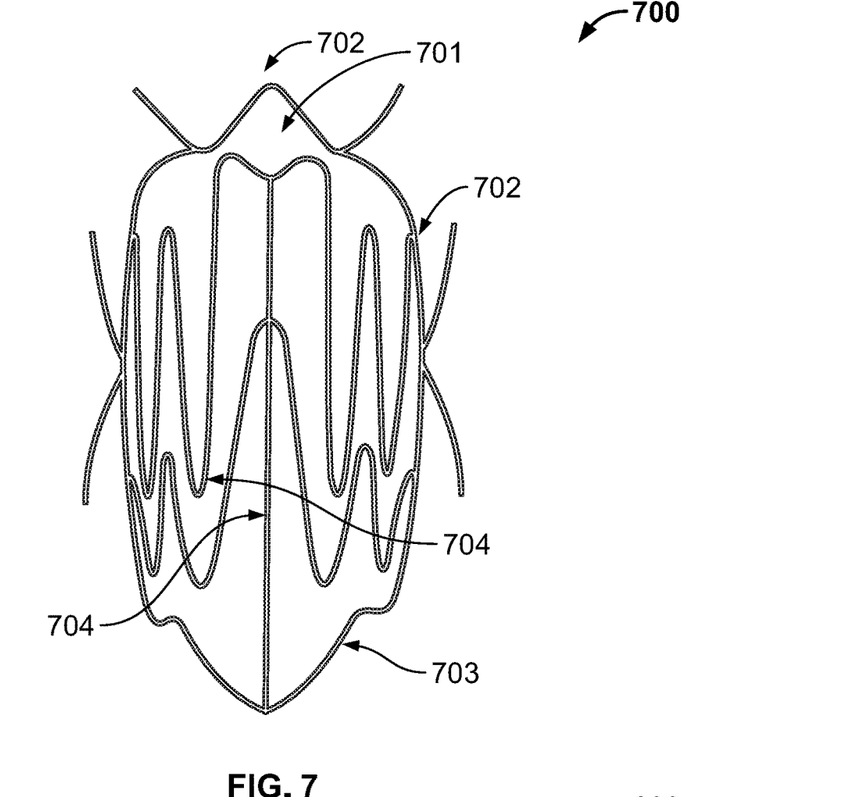
FIG. 7 is a top view of the flap portion of the parent vessel stent shown in FIG. 5.

FIG. 7 shows the top view of the flap area 700 (FIG. 5 at 502). The daughter vessel guide wire is introduced at introduction site 701 just proximal to the radio-opaque marker 702. The folded struts and spine of the "flap" 704 are deployed by a balloon in the daughter vessel and provide coverage for the proximal edge of the ostium of the daughter vessel. Strut 703 forms a perimeter around the ostium of the daughter vessel. Some of these structures are shown again in FIGS. 8 and 9 below.

Figure 8:
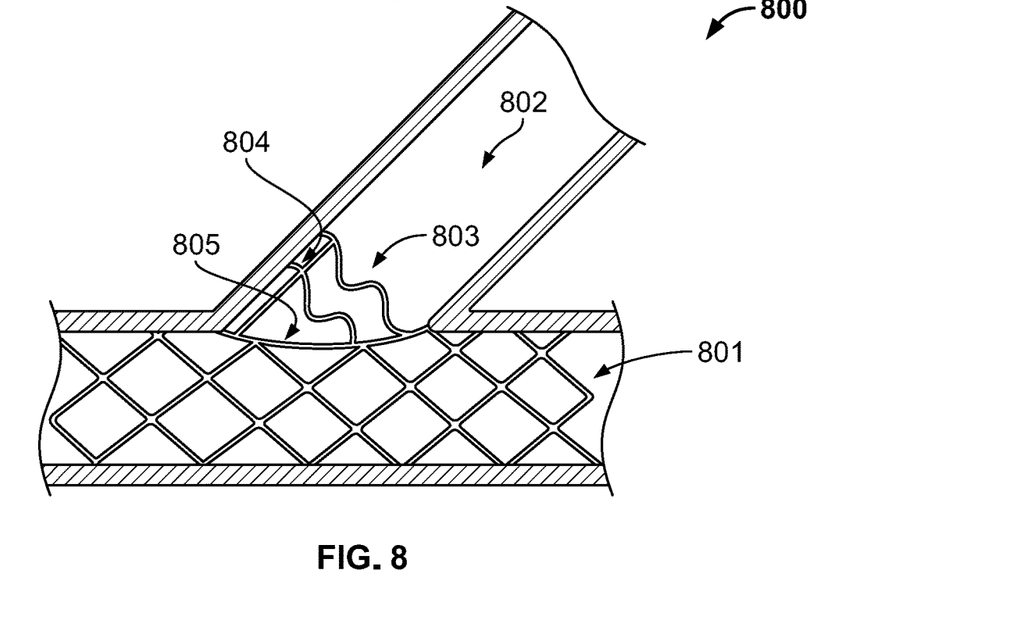
FIG. 8 is a diagram showing stent in parent vessel with flap extended, showing strut arrangement.

FIG. 8 shows parent vessel stent system 800 with stent deployed in the parent vessel 801 with flap extended into the ostium of the daughter vessel 802. Struts 803 and 804 provide coverage to the ostium of the daughter vessel and strut 805 forms the perimeter around the ostium.

Figure 9:
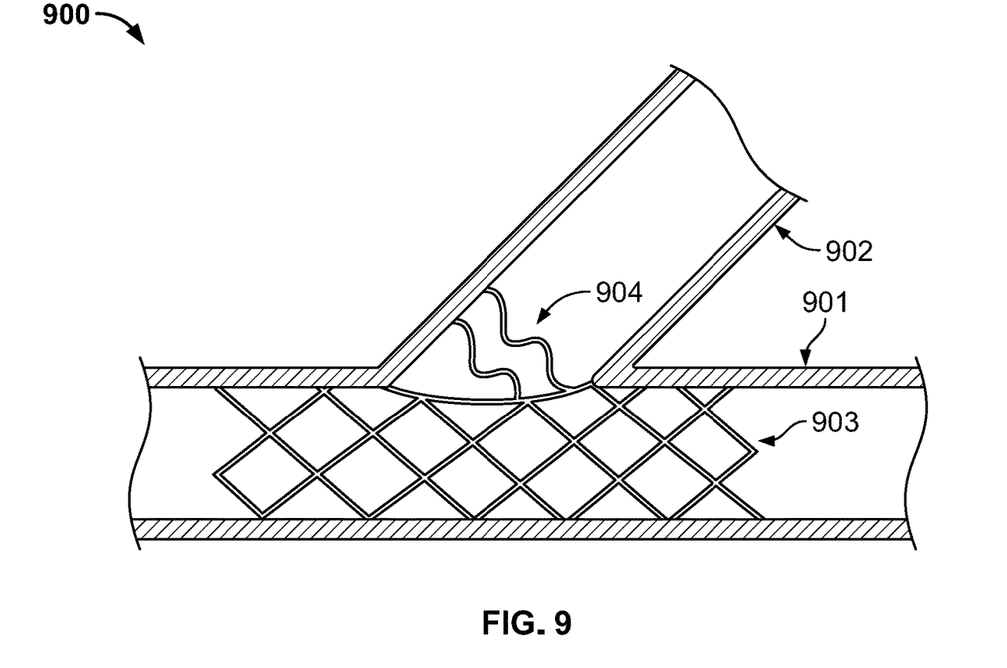
FIG. 9 is a diagram showing stent in parent vessel with flap extended.

FIG. 9 shows parent vessel stent system 900 with parent vessel 901 stent 903 deployed with flap extended 904 into the ostium of the daughter vessel 902.

Figure 10:
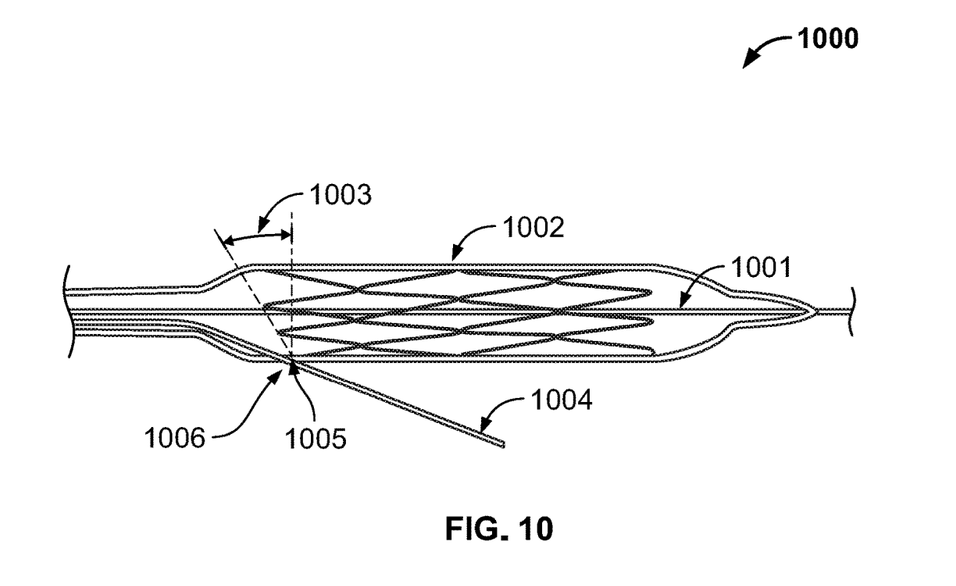
FIG. 10 is a schematic diagram of a daughter vessel stent system according to an embodiment of the present invention.

FIG. 10 shows the basic structure of the daughter vessel (side branch) system 1000 with daughter vessel stent 1002. Here the guide wire from the daughter vessel 1001 is coaxial in the center. The proximal edge of the stent is angled 1003 for coverage of the ostium in conjunction with the flap of the parent vessel stent. The guide wire from the parent vessel 1004 is introduced at side hole 1005 just proximal to the short side of the stent (i.e. opposite angled edge 1003). The radio-opaque marker 1006 helps with positioning of the stent.

Figure 11:
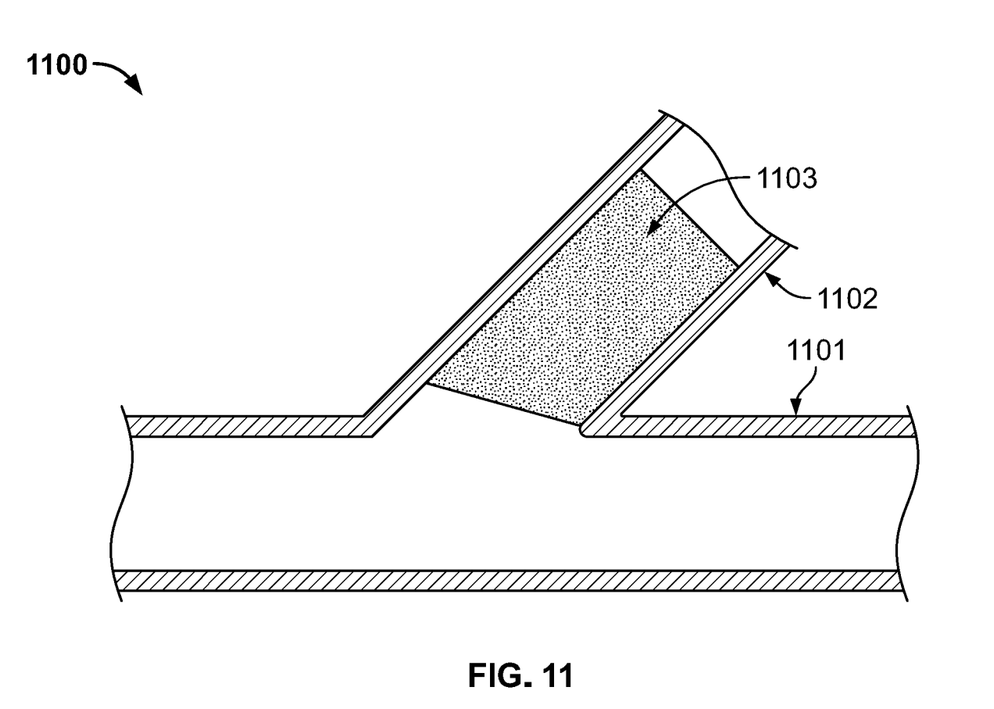
FIG. 11 is a simplified vessel diagram showing deployed side branch (daughter vessel) stent in relation to parent vessel.

FIG. 11 shows the daughter vessel system 1100 with deployed side branch (daughter vessel) 1102 stent 1103 in relation to the parent vessel 1101.

Following FIGS. 12 through 17 show the deployment sequence of current system.

Figure 12:
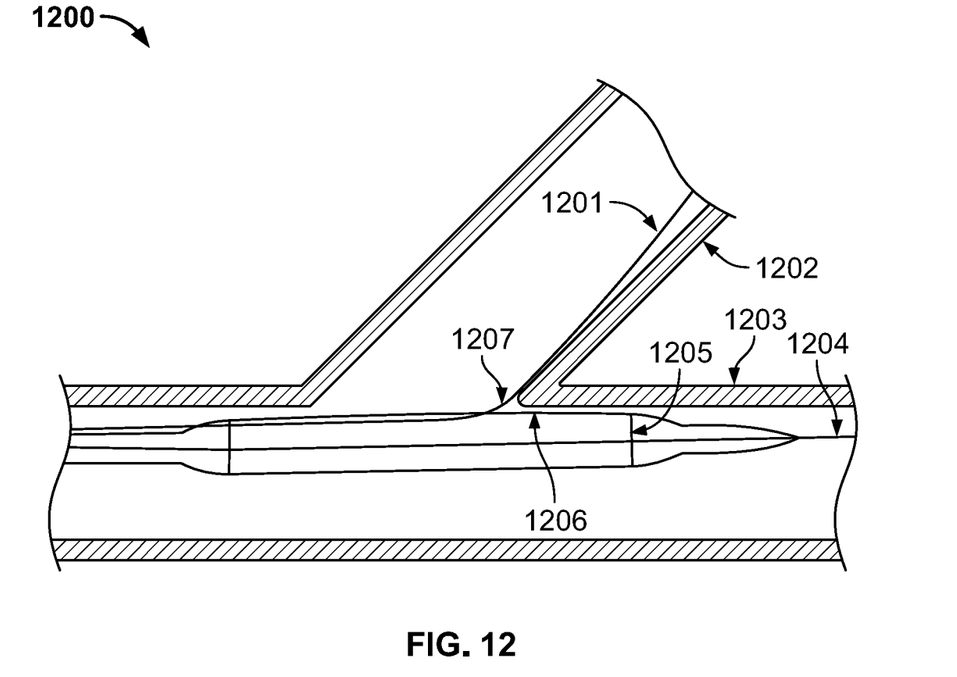
FIG. 12 is a simplified vessel diagram showing a first stage of deployment process according to an embodiment of the present method (positioning of parent vessel stent).

FIG. 12 shows positioning 1200 of parent vessel (main vessel) 1203 stent 1205 across the daughter vessel 1202. The parent vessel guide wire 1204 is coaxial and guide wire from the daughter vessel 1201 is introduced through the flap in the parent vessel stent (region 502 shown in FIG. 5). The stent is then advanced till the daughter vessel guide wire 1201 is against the distal edge of the ostium 1207. Placement is also assisted by observing and placing the radio-opaque marker 1206 just beyond the ostium of the daughter vessel.

Figure 13:
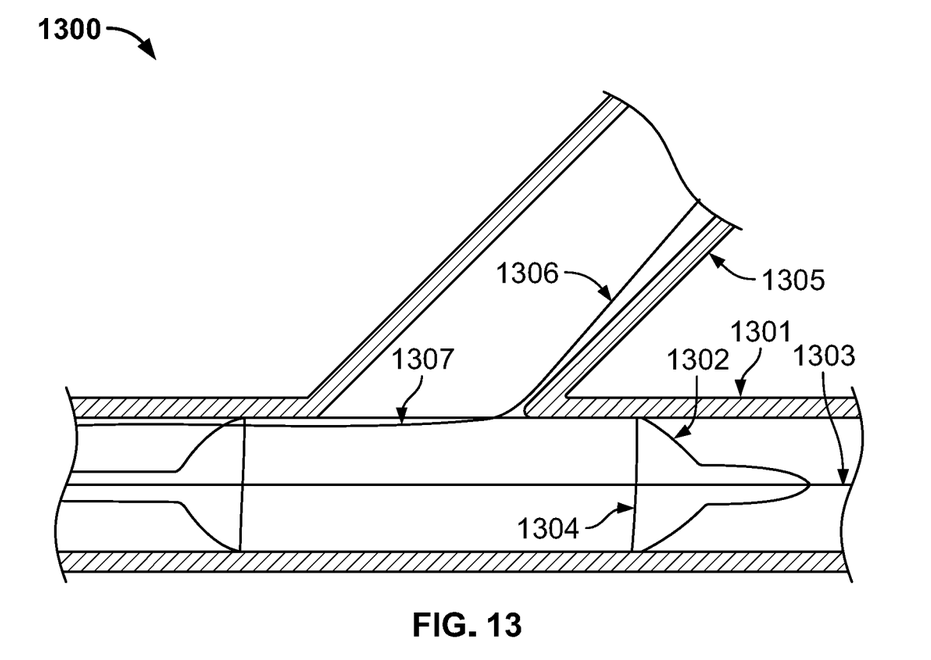
FIG. 13 is a simplified vessel diagram showing a second stage of the deployment process (balloon inflation of parent vessel stent in the parent vessel).

FIG. 13 shows the deployment 1300 of parent vessel 1301 stent 1304 coaxially over the guide wire 1303 with balloon inflation 1302; the daughter vessel 1305 guide wire 1306 is retained and, being on the inside of the stent in area 1307, is not trapped.

Figure 14:
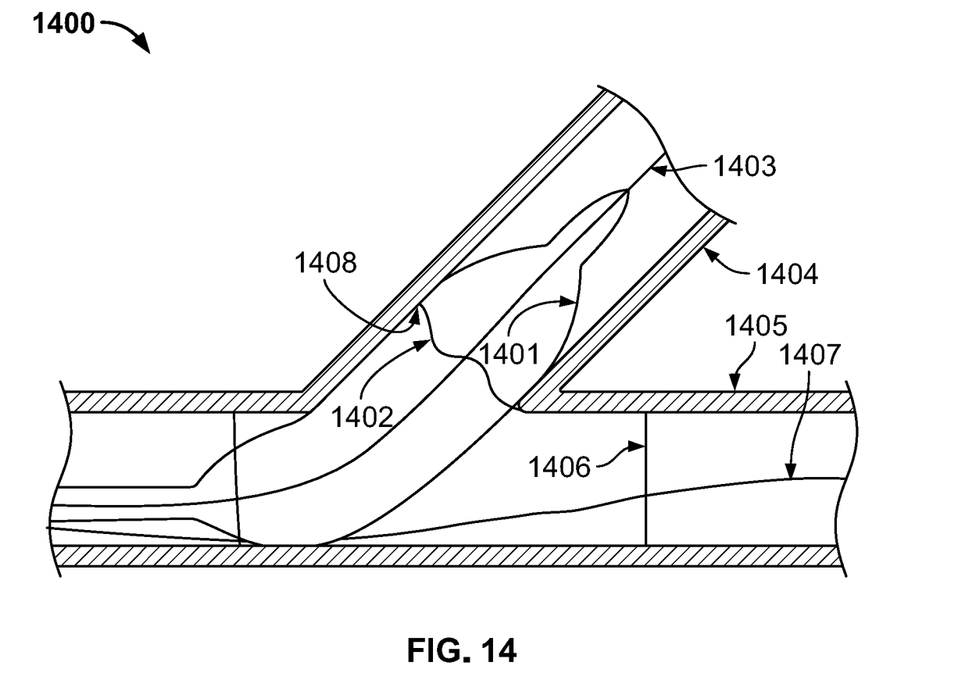
FIG. 14 is a simplified vessel diagram showing a third stage of the deployment process (balloon opening of flap in parent vessel stent into daughter vessel).

FIG. 14 shows a further deployment 1400 of the parent vessel stent using standard angioplasty balloon 1401 which is used in this case to raise/extend the flap portion 1402 of the parent vessel 1405 stent 1406. The balloon is placed coaxially over the guide wire 1403 in the daughter vessel 1404. The guide wire 1407 in the parent branch is retained. The radio-opaque marker 1408 on the edge of the flap shows the area of coverage on the proximal edge of the ostium of the daughter branch.

Figure 15:
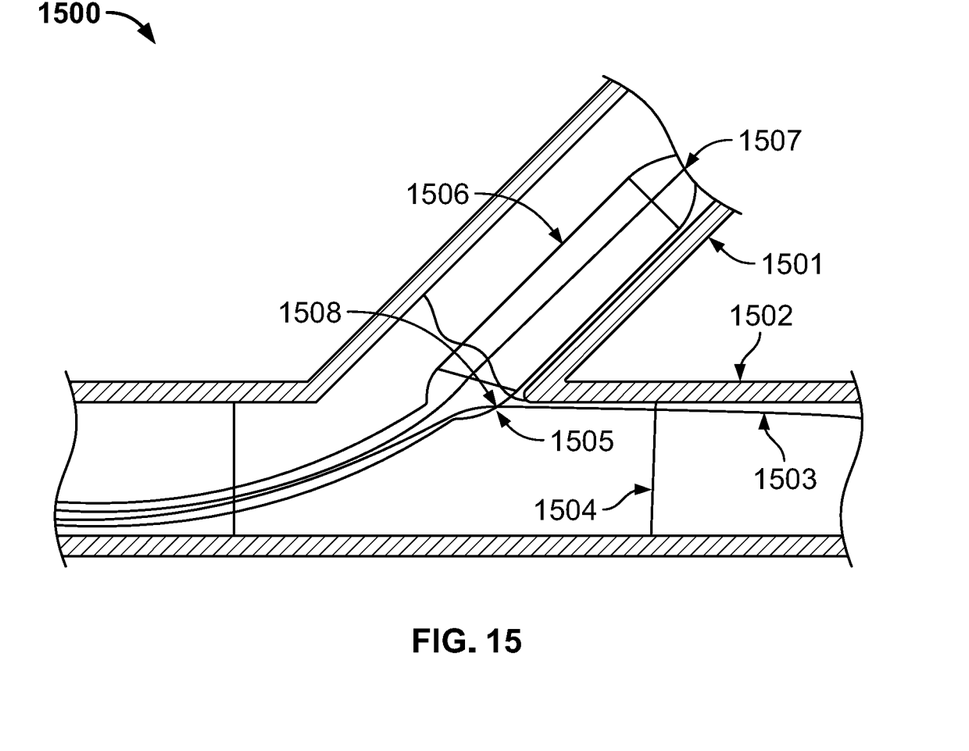
FIG. 15 is a simplified vessel diagram showing a fourth stage of the deployment process (positioning of daughter vessel stent through flap in parent vessel stent).

FIG. 15 shows positioning 1500 of the daughter vessel 1501 (side-branch) stent 1506 at the ostium, using the parent vessel guide wire 1503 and radio-opaque marker 1505 on the stent as guides. The parent vessel guide wire 1503 is introduced through the "side-hole" 1508 in the stent catheter located just proximal to the short side of the stent (1005 FIG. 10) while the daughter vessel guide wire 1507 is coaxial with the daughter vessel stent 1506. The daughter vessel stent 1506 is advanced through the flap of the parent vessel stent 1504, as far as permitted by the guide wire in the parent vessel. Positioning is also assisted by the radio-opaque marker 1505.

Figure 16:
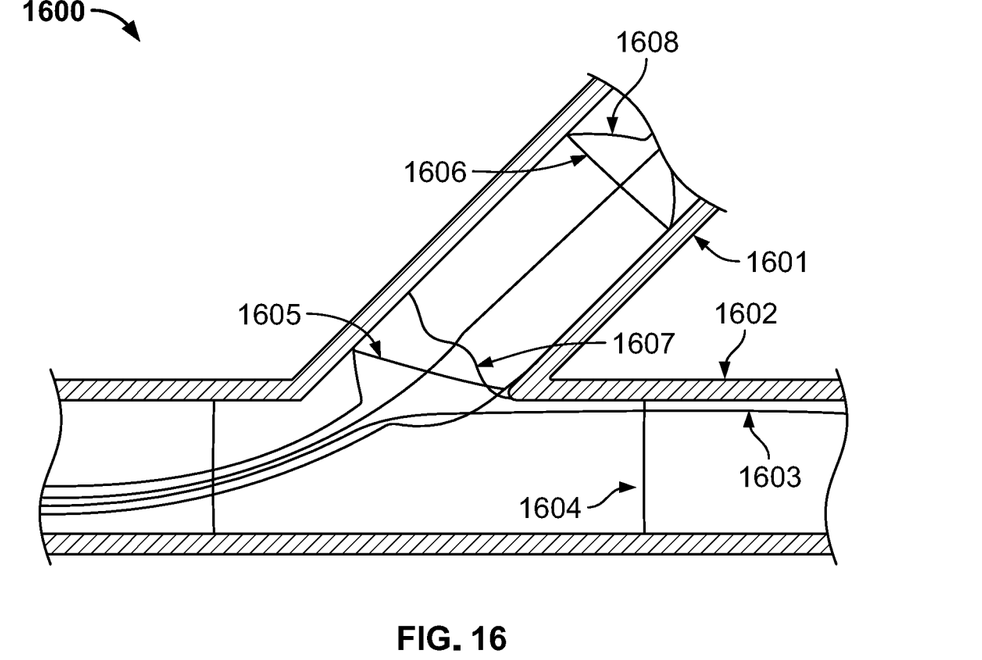
FIG. 16 is a simplified vessel diagram showing a fifth stage of the deployment process (balloon inflation of daughter vessel stent in daughter vessel).

FIG. 16 shows deployment 1600 of the daughter vessel 1601 stent 1606 via balloon 1608. Parent vessel guide wire 1603 is retained. The overlap 1605 of the angled edge with the flap 1607 of the parent vessel stent 1604 provides total coverage of the proximal edge of the ostium.

Figure 17:
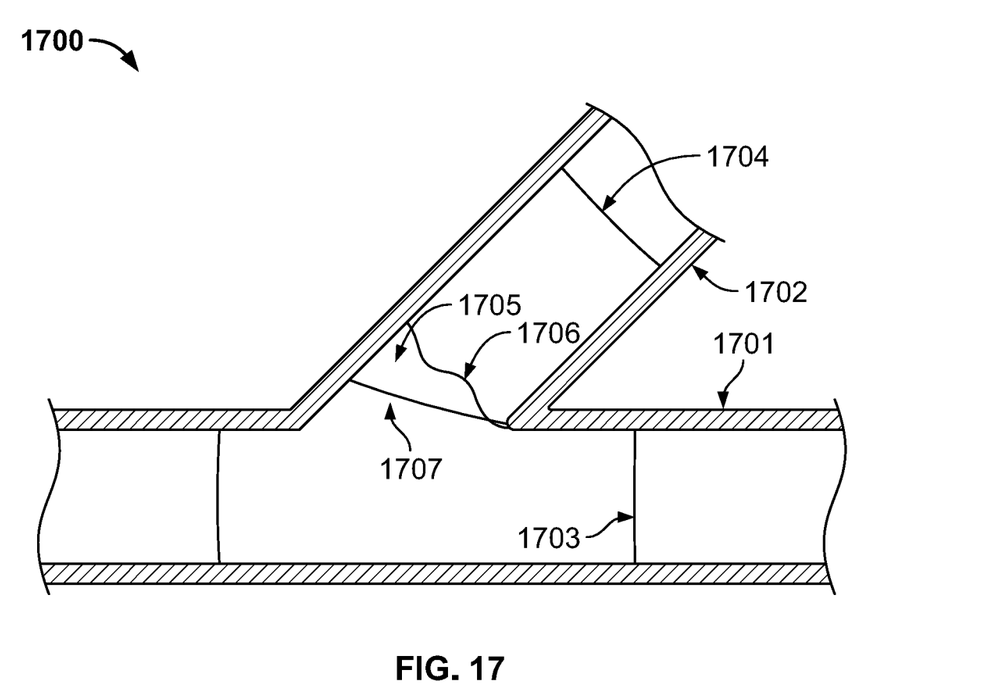
FIG. 17 is a simplified vessel diagram showing a sixth and final stage after removal of balloon and guide wires (showing overlap between daughter vessel stent and parent vessel stent to provide complete coverage of the bifurcation area without unopposed struts or jailing across the ostium).

FIG. 17 shows the final deployed state of the bifurcation stent system 1700. The overlap segment 1705 between the flap 1706 of the parent vessel 1701 stent 1703 and the angled proximal edge 1707 of the daughter vessel 1702 stent 1704 allows for adequate coverage of the ostium of the daughter vessel. The system provides such coverage over a wide range of "take-off" angles between the parent and daughter vessels.

The intent of the application is to cover all practical combinations and permutations. The above examples are not intended to be limiting, but are illustrative and exemplary.

The examples noted here are for illustrative purposes only and may be extended to other implementations. While several embodiments are described, there is no intent to limit the disclosure to the embodiment(s) disclosed herein. On the contrary, the intent is to cover all practical alternatives, modifications, and equivalents.

What is claimed is:

1. A stent system for stenting a bifurcated vessel structure having a parent vessel and a daughter vessel, the daughter vessel branching from the parent vessel at an angle, the daughter vessel having an ostium where it joins the parent vessel, the ostium having a proximal edge and a distal edge, the stent system comprising:

a parent vessel guide wire and a daughter vessel guide wire;

a parent vessel stent having a substantially tubular body that is configured to be deployed into the parent vessel by loading the parent vessel stent on both wires, such that the parent vessel guide wire is substantially coaxial with the parent vessel stent, and such that the daughter vessel guide wire runs generally inside the parent vessel stent along its daughter vessel luminal side, the body having an integrally formed angular flap that can only be opened to extend into the daughter vessel in a configuration that does not form a collar around an ostium of the daughter vessel, the angular flap having an introduction site through which the daughter vessel guide wire extends; and a daughter vessel stent having a substantially tubular body that is configured to be into the daughter vessel by loading the daughter vessel stent on the daughter vessel guide wire after the parent vessel stent has been deployed and its side flap has been opened, such that the daughter vessel guide wire is generally coaxial with the daughter vessel stent and passes through the length of the daughter vessel stent, the daughter vessel stent having a side hole through which the parent vessel guide wire extends, the daughter vessel guide wire and the parent vessel guide wire cooperating to allow the daughter vessel stent to be advanced into a position where the daughter vessel stent is at the distal edge of the ostium of the daughter vessel, the daughter vessel stent having an angled tail portion configured to overlap with the flap of the parent vessel stent without extending into the parent vessel when both stents are deployed in the vessel structure.

2. The stent system of claim 1, wherein the parent vessel stent includes a radio-opaque marker proximate to the introduction site of the parent vessel stent.

3. The stent system of claim 2, wherein the flap includes at least one radio-opaque marker.

4. The stent system of claim 1, wherein the parent vessel stent has a spine which also extends along a central portion of the flap.

5. The stent system of claim 1, wherein the parent vessel stent is pre-loaded with a balloon for deployment of the parent vessel stent.

6. The stent system of claim 1, wherein at least one of the parent vessel stent or the daughter vessel stent contains a drug, or is configured to elute a drug.

7. The stent system of claim 1, wherein the daughter vessel stent includes a radio-opaque marker proximate to the side hole of the daughter vessel stent.

8. The stent system of claim 7, wherein the side hole is defined radially opposite the angled tail portion of the daughter vessel stent.

9. A method of stenting a bifurcated vessel structure, the structure having a parent vessel and a daughter vessel, the daughter vessel branching from the parent vessel at an angle, the daughter vessel having an ostium where it joins the parent vessel, the ostium having a proximal edge and a distal edge, the method comprising:
   inserting a parent vessel guide wire and a daughter vessel guide wire into the parent and daughter vessels, respectively;
   loading a parent vessel stent on both wires, such that the parent vessel guide wire is substantially coaxial with the parent vessel stent; and such that the daughter vessel guide wire runs generally inside the parent vessel stent along its daughter vessel luminal side and extends through an introduction site in an integrally formed side flap in the parent vessel stent;
   positioning the parent vessel stent with the daughter vessel guide wire at the distal edge of the daughter vessel ostium;
   deploying the parent vessel stent with a first balloon;
   deploying the side flap of the parent vessel stent into the ostium of the daughter vessel using a second balloon mounted on the daughter vessel guide wire, the side flap being configured such that it cannot form a collar around the ostium of the daughter vessel;
   loading a daughter vessel stent on the daughter vessel guide wire, such that the daughter vessel guide wire is generally coaxial with the daughter vessel stent and passes through the length of the daughter vessel stent, and inserting the parent vessel guide wire such that the parent vessel guide wire runs through a side hole in the daughter vessel stent;
   advancing the daughter vessel stent by cooperating of the daughter vessel guide wire and the parent vessel guide wire to position the daughter vessel stent at the distal edge of the ostium of the daughter vessel; and
   deploying the daughter vessel stent with a third balloon;
   wherein the flap of the deployed parent vessel stent and an angled side wall of the deployed daughter vessel stent overlap and are apposed at least in part with the proximate edge of the ostium without the daughter vessel stent extending into the parent vessel.

10. The method of claim 9, further comprising predilating one or both vessels prior to inserting the parent vessel guide wire.

11. The method of claim 9, further comprising removing plaque from one or both vessels prior to inserting the parent vessel guide wire.

12. The method of claim 9, further comprising performing a kissing balloon inflation with a fourth balloon after deploying the daughter vessel stent for further shaping of the bifurcation.

* * * * *